United States Patent [19]

Rescalli et al.

[11] 4,031,157

[45] June 21, 1977

[54] METHOD FOR REMOVING ACETYLENIC COMPOUNDS FROM SATURATED, OLEFINIC AND DIENIC HYDROCARBONS OR MIXTURES THEREOF

[75] Inventors: Carlo Rescalli; Antonio Pacifico, both of San Donato Milanese, Italy

[73] Assignee: Snam Progetti S.p.A., San Donato Milanese, Italy

[22] Filed: May 21, 1975

[21] Appl. No.: 579,691

[30] Foreign Application Priority Data

May 21, 1974 Italy .................................. 23011/74
Mar. 21, 1975 Italy .................................. 21517/75

[52] U.S. Cl. ........................ 260/676 R; 260/677 A; 260/681.5 R

[51] Int. Cl.² ........................................... C07C 7/04

[58] Field of Search ................ 260/677 A, 681.5 R, 260/676 R

[56] References Cited

UNITED STATES PATENTS 2,917,563  12/1959  Dye ................................. 260/677 A
3,170,000  2/1965  Verdol ........................... 260/677 A Primary Examiner—Herbert Levine
Attorney, Agent, or Firm—Ralph M. Watson

[57] ABSTRACT

The present invention provides a novel process for the separation of acetylenic compounds from saturated, olefinic and dienic hydrocarbons by etherifying the acetylenic compounds with an alcohol or a glycol in the presence of an acid ion-exchange resin containing mercuric ions.

1 Claim, 1 Drawing Figure

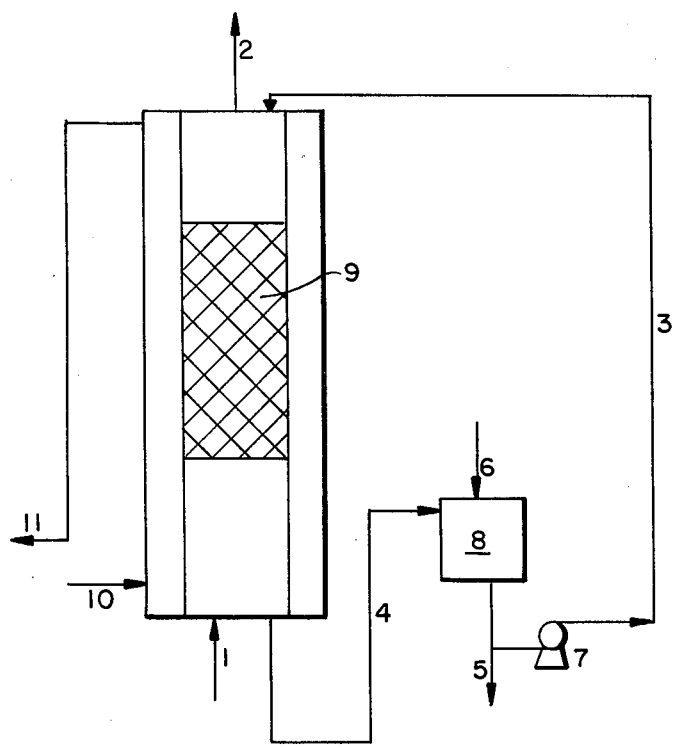

METHOD FOR REMOVING ACETYLENIC COMPOUNDS FROM SATURATED, OLEFINIC AND DIENIC HYDROCARBONS OR MIXTURES THEREOF

The present invention relates to a method for removing acetylenic compounds from saturated, olefinic and dienic hydrocarbons or mixtures thereof.

More particularly the present invention concerns a method for removing propyne, 1 butyne, 2 butyne, vinylacetylene, diacetylene, acetylene from a mixture of butadiene, propylene, ethylene alone or in mixture with other saturated and/or olefinic hydrocarbons having the same number of carbon atoms.

Still more particularly the present invention concerns a method:
1. for removing propyne, 1 butyne, vinylacetylene and/or diacetylene from butadiene alone or in mixture with other saturated and/or olefinic hydrocarbons having the same number of carbon atoms; (2). for removing propyne from propylene alone or in mixture with other saturated and/or olefinic hydrocarbons having the same number of carbon atoms; (3) for removing acetylene from ethylene alone or in mixture with ethane.

It is known that for most utilizations the saturated, olefinic and in particular dienic hydrocarbons must be free from acetylenic compounds; for instance the content of said products in the butadiene monomer must be ≤ 50 p.p.m. and this because of their poisoning action on the polymerization catalysts.

Several methods were proposed and are at present utilized for removing acetylenic compounds as far instance:

a. selective hydrogenation
b. fractional distillation
c. extractive distillation in presence of suitable solvents.

Said methods, alone or in combination, permit to reach the specification of acetylenic compounds but request substantially high operative costs and/or particular apparatuses and therefore high investment costs. It has been found that it is possible to eliminate completely the acetylenic compounds without using the operations of the known art obtaining at the same time remarkable economical advantages.

Object of the present invention is a process for removing acetylenic compounds from the aforesaid streams consisting in etherifying selectively said acetylenic compounds with an alcohol particularly and preferably methanol or with a glycol, particularly and preferably monoethylene glycol or diethylene glycol in presence of a acid ion-exchange resin containing mercuric ions.

The ethers are subsequently removed by a simple and economical rectification operation.

The used ion-exchange resin, as above said, has an acid character and preferably contains sulphonic groups ($-SO_3H$ supported on resins for instance polystyrene, divinyl benzene or phenolic resins), but use can be made also of resins containing $-COOH$ groups.

The mercuric ions can be added to the resin in the form of mercury salts, particularly in the form of mercury nitrate or acetate; the content of $Hg^{++}$ ions of the resin can be also lower than the total cationic capacity of the resin.

The hydrocarbons which can be purified in accordance with the present invention are paraffinic and olefinic hydrocarbons and conjugated dienes (in particular butadiene, propylene and ethylene).

Etherification can be carried out within a wide range of temperatures but it is advantageous to work within the range of from $-20°$ to $80°$ C and still more advantageously within the range of from $+20°$ to $60°$ C, utilizing preferable a conventional column containing ion-exchange resin; the working pressure is chosen preferably in such a way to maintain in liquid phase the stream at the reaction temperature.

The contact time is in the range of from 2 to 30 minutes.

It is opportune to operate in presence of a stoichiometric excess of the alcohol or glycol with respect to the acetylenic products; in practice it is convenient to work with a molar ratio alcohol/(total acetylenic compounds) = 1.05–2.0.

It has been found moreover that in presence of the same ion-exchange resin containing mercuric ions above described the acetylenic compounds react with whatsoever kind of compounds of the R—OH type wherein R is a alkyl, acyl, aryl, cycloalkyl radical forming addition products in quantitative way, said products being then removed simply by distillation, analogously to what described for ethers.

In particular the aforesaid reactions are vinylation or etherification reactions. It is to be observed that all the aforesaid reactions can be carried out indifferently in gaseous phase or in liquid phase.

We shall now give same examples in order to illustrate in a better way the invention without limiting in any case the same.

EXAMPLE 1

To 400 cc of an aqueous solution at 3% by weight of $Hg(NO_3)_2 \cdot H_2O$ we added 100 grams of a resin of the type Amberlist 15, containing acid groups of the type $— SO_3H$.

The mixture was kept under stirring for 1 hour, then was filtered under vacuum and the resin was repeatedly washed with methanol always under vacuum.

A portion of the resin treated as above-said was introduced into a reactor of 20 cc volume maintained at 40° C by means of a thermostatic circuit. Into the same reactor we continuously pumped, working at 5.0 ata, 100 cc/h of butadiene containing 1.05% by weight of butyne, 1,350 ppm by weight of vinylacetylene and methanol in such amount to have a alcohol/(total acetylenic compounds) ratio 1.7 moles/mole.

The content of both acetylenic compounds determined in the liquid samples withdrawn from the exit of the reactor was ≤ 10 ppm by weight.

EXAMPLE 2

Into the same reactor indicated in example 1, working at 30° C and at pressure of 4 ata, we continuously pumped 200 cc/h of butadiene containing 1.2% by weight of propyne, 150 ppm by weight of vinylacetylene, 200 ppm by weight of 2 butyne and methanol in such amount to have a alcohol/(total acetylenic compounds) ratio equal to 1.25 moles/mole.

The content of the three acetylenic compounds determined in the liquid samples withdrawn from the exit of the reactor was ≤ 10 ppm by weight.

EXAMPLE 3

Into the same reactor indicated in example 1, working at 30° C and at a pressure of 10 ata we continuously pumped 100 cc/h of propylene containing 0.5% by weight of propyne and methanol in such amount to have the alcohol/(acetylenic compound) ratio = 1.15 moles/mole.

The content or propyne determined in the liquid samples at the exit from the reactor was ≤ 10 ppm by weight.

EXAMPLE 4

Addition of Carboxylic Acids to Acetylenic Compounds

Into the same reactor described in example 1 working at 50° C and pressure of 30 ata with a resin prepared in the same way as that shown in the same example and washed at last with glacial acetic acid we continuously pumped 50cc/h of propylene containing 0.5% by weight of propyne and acetic acid in such amount to have a acetic acid/(acetylenic compound) ratio equal to 2.0 moles/mole.

The content of propyne present in the liquid samples withdrawn from the exit of the reactor was ≤ 10 ppm by weight.

EXAMPLE 5

We worked with a suitable reactor 9 of 150 cc of volume thermostated and provided with lines for (see enclosed FIG. 1):

a. introducing into the bottom in gaseous phase, the hydrocarbon stream 1 rich of acetylenic compounds.
b. discharging from the top, in gaseous phase, the same hydrocarbon stream 2 after treatment.
c. feeding to the top a liquid stream which can be constituted by alcohol alone or a mixture of alcohol and ethers (line 3).
d. discharging from the bottom, by means a siphon 4, into a tank 8 a liquid stream constituted by alcohol and ethers.

Said last stream was totally or partially recycled by means of pump 7 into the reactor through line 3; the portion 5 which was possibly drained was replaced by an equal amount of fresh alcohol 6.

Into the aforesaid reactor 9 we fed 50 g of the precedingly prepared resin (see example 1), which was subsequently completely wetted with methanol (this last had to be discharged through siphon 4); into the same reactor maintained at 50° C by means of a special thermostatic circuit (the thermostating liquid entered through 10 and came out through 11) and at a pressure of 1 ata we then fed through line 1, 20 g/h of propylene stream containing 0.1% of propyne, while about 50 g/h of the liquid stream discharged from the bottom through line 4 were totally recycled to the top of the reactor through line 3.

The content of propyne present in the gaseous samples withdrawn from the exit of the reactor was ≤ 10 ppm by weight.

What we claim is:

1. A method for removing acetylenic compounds from saturated, olefinic or dienic hydrocarbons or their mixtures which comprises removing said acetylenic compounds from said saturated, olefinic or dienic hydrocarbons or their mixtures by etherification with an alcohol or a glycol in presence of an acid ion-exchange resin, containing mercuric ions and subsequently removing the produced ethers by distillation.

* * * * *